United States Patent [19]
Peterson et al.

[11] Patent Number: 5,312,577
[45] Date of Patent: May 17, 1994

[54] METHOD FOR MANUFACTURING AN AMPULE

[75] Inventors: Steven F. Peterson, West Linn; John W. Ashley, Hillsboro; Victor L. Bartholomew, Tigard; James P. Casey, Sr., Forest Grove, all of Oreg.; Charles N. McKinnon, Jr., Laguna Niguel, Calif.

[73] Assignee: Bioject Inc., Portland, Oreg.

[21] Appl. No.: 880,249

[22] Filed: May 8, 1992

[51] Int. Cl.⁵ ............................................. B29C 45/17
[52] U.S. Cl. ................................. 264/154; 264/328.1; 425/577
[58] Field of Search ............ 264/154, 161, 162, 328.1; 425/577, 468; 249/149

[56] References Cited

U.S. PATENT DOCUMENTS

| | | | |
|---|---|---|---|
| 2,087,470 | 7/1937 | Davidson et al. | 264/161 |
| 2,387,034 | 10/1945 | Milano | 264/161 |
| 2,737,946 | 3/1956 | Hein, Jr. | |
| 3,855,380 | 12/1974 | Gordon et al. | 264/161 |
| 3,945,383 | 3/1976 | Bennett et al. | |
| 4,126,291 | 11/1978 | Gilbert et al. | 425/468 |
| 4,284,459 | 8/1981 | Patel et al. | 264/138 |
| 4,307,059 | 12/1981 | Cambio | 425/503 |
| 4,360,330 | 11/1982 | McFarlane | 425/122 |
| 4,649,616 | 3/1987 | Bricker | |
| 4,705,877 | 6/1988 | McFarlane | 425/577 |
| 4,925,128 | 5/1990 | Brody | 264/328.1 |
| 5,078,690 | 1/1992 | Ryan | 222/323 |
| 5,102,608 | 4/1992 | Frencken et al. | 264/328.1 |

*Primary Examiner*—Jan H. Silbaugh
*Assistant Examiner*—Christopher A. Fiorilla
*Attorney, Agent, or Firm*—Lyon & Lyon

[57] ABSTRACT

A method and mold for making an ampule for a needleless or jet injector device. The tip of a core pin is guided into a clearance hole sufficiently large to prevent the tip from hitting the mold cavity. Plastic is injected into the mold and flows into the space between the core pin tip and the clearance hole forming a vestigial nozzle pilot cylinder around and over the ampule nozzle. The ampule is removed from the mold and the vestigial nozzle pilot cylinder is removed to form a finished ampule. A core pin tip is made of drawn wire or is separately replaceable on the core pin. A nozzle of an ampule is cast in place. An ampule is molded with an enlarged nozzle and a separate orifice is installed in the ampule to provide the desired nozzle opening.

5 Claims, 6 Drawing Sheets

METHOD FOR MANUFACTURING AN AMPULE

BACKGROUND OF THE INVENTION

Needleless or jet injectors typically use pressurized gas to accelerate a plunger into an ampule holding liquid injectant, thereby causing the injectant to flow out of the ampule with sufficient pressure or velocity to penetrate the skin of the patient. Ampules used with needleless injectors are preferably disposable, must be strong enough to withstand the stresses of injection, and must be made from a biocompatible material. In addition, ampules are preferably transparent to allow for visual inspection of their contents.

Thermoplastic injection molding is preferred for manufacturing ampules because there are numerous thermoplastics available which are biocompatible, transparent, strong, and have good molding characteristics. In addition, in a typical injection molding process for manufacturing ampules, an injection cycle can be completed in less than one minute, and multiple molds or cavities allow for proportionally lower costs, a significant factor for disposable ampules. The injection molding process also can achieve smooth contours and transitions within the ampule, which provides for more efficient liquid injectant flow during injection. Sufficient manufacturing tolerances can also be economically maintained with thermoplastic injection molding, whereas attempting to achieve the same result with machining or drilling would be difficult. Thermoplastic injection molding also results in ampules free of particulate matter, whereas machining and drilling processes create particles that must be removed in a separate process which increases cost and complexity.

Molds used to produce ampules are generally constructed of two primary elements, a cavity housing and a core pin. The cavity housing forms the external surfaces of the ampule, while the core pin forms the internal surfaces, including the critical nozzle section.

Frequently, in thermoplastic injection molding production of ampules, the core pin tip fractures or breaks during the molding process. Bending stresses on the core pin tip can be introduced when the tip of the core pin is inserted into a pilot hole, as the mold is closed. Bending of the core pin tip also occurs when the hot liquid plastic is injected into the mold. The pressure of flowing plastic is not uniform on all sides of the pin, resulting in deformation of the core pin tip. This produces bending fatigue of the tip and eventual breakage.

Breakage also occurs when the mold is opened and the ampule is removed after the molten plastic has solidified. The core pin tip becomes very hot during the injection of the plastic because it is not cooled by water as are other surf aces of the mold. This can result in welding of the plastic to the steel pin tip. Although the preferred ampule molding material, high strength polycarbonate, has good clarity and strength, it unfortunately also sticks to the mold surfaces more than most other plastics.

The force required to shear a welded plastic ampule from a core pin is proportional to the diameter of the pin, while the strength of the pin is proportional to the diameter squared. The stress on the pin during removal of the ampule f rom the mold is therefore inversely proportional to the diameter of the pin. Hence, there is a limit on how small the core pin tip can be before it cannot be withdrawn f rom the part without breaking, and with smaller diameter core pin tips, the breakage rate is higher. The rate of breakage of the core pin tip is inversely related to the diameter of the ampule nozzle. For ampules having 0.008 inch diameter nozzles, the breakage rate is low and the molding process is reliable enough to produce parts on an ongoing basis. On the other hand, for ampules with 0.004 inch diameter nozzles, the breakage rate is very high and makes the injection molding process not cost effective because the process must be stopped and the mold disassembled and repaired with each core pin tip breakage.

The pilot hole typically has a 0.0015 inch clearance gap around the core pin tip. This very close fit prevents flashing of the plastic into the clearance gap. However, if the core pin tip strikes the edge of the pilot hole during closure of the mold, the tip will bend and/or break. The dimensional control of the pilot hole in the cavity housing-core pin registration in a multiple cavity tool, with thermal distortion, approaches the limits of the current art in mold making and injection molding. Accordingly, there is a need for an improved method for manufacturing ampules.

SUMMARY OF THE INVENTION

The present invention is directed to a tool and methods for manufacturing ampules. To this end, a core pin tip is guided into a clearance hole in the cavity housing that is sufficiently large to ensure that the core pin tip will not hit the side of the clearance hole. The excess cylinder of material formed in the clearance hole during injection of the plastic is cut off to open up the nozzle of the ampule, after the ampule is removed from the mold. The core pin tip can also be made of high strength wire, to resist breakage, or can be made replaceable. Also to the this end, the ampule nozzle may be cast in a secondary operation, or the nozzle can be formed by inserting or attaching a separate orifice to the ampule.

Accordingly, it is an object of the invention to provide improved methods and apparatus for manufacturing ampules.

BRIEF DESCRIPTION OF THE DRAWINGS

Other objects and features of the present invention will become apparent f rom the following detailed description taken in connection with the accompanying drawings, which disclose several embodiments of the invention. It is to be understood, however, that the drawings are designed for the purpose of illustration only and are not intended as a definition of the limits of the invention.

In the drawings, wherein similar reference characters denote similar elements throughout the several views.

DETAILED DESCRIPTION OF THE PREFERRED EMBODIMENTS

Figure 1:
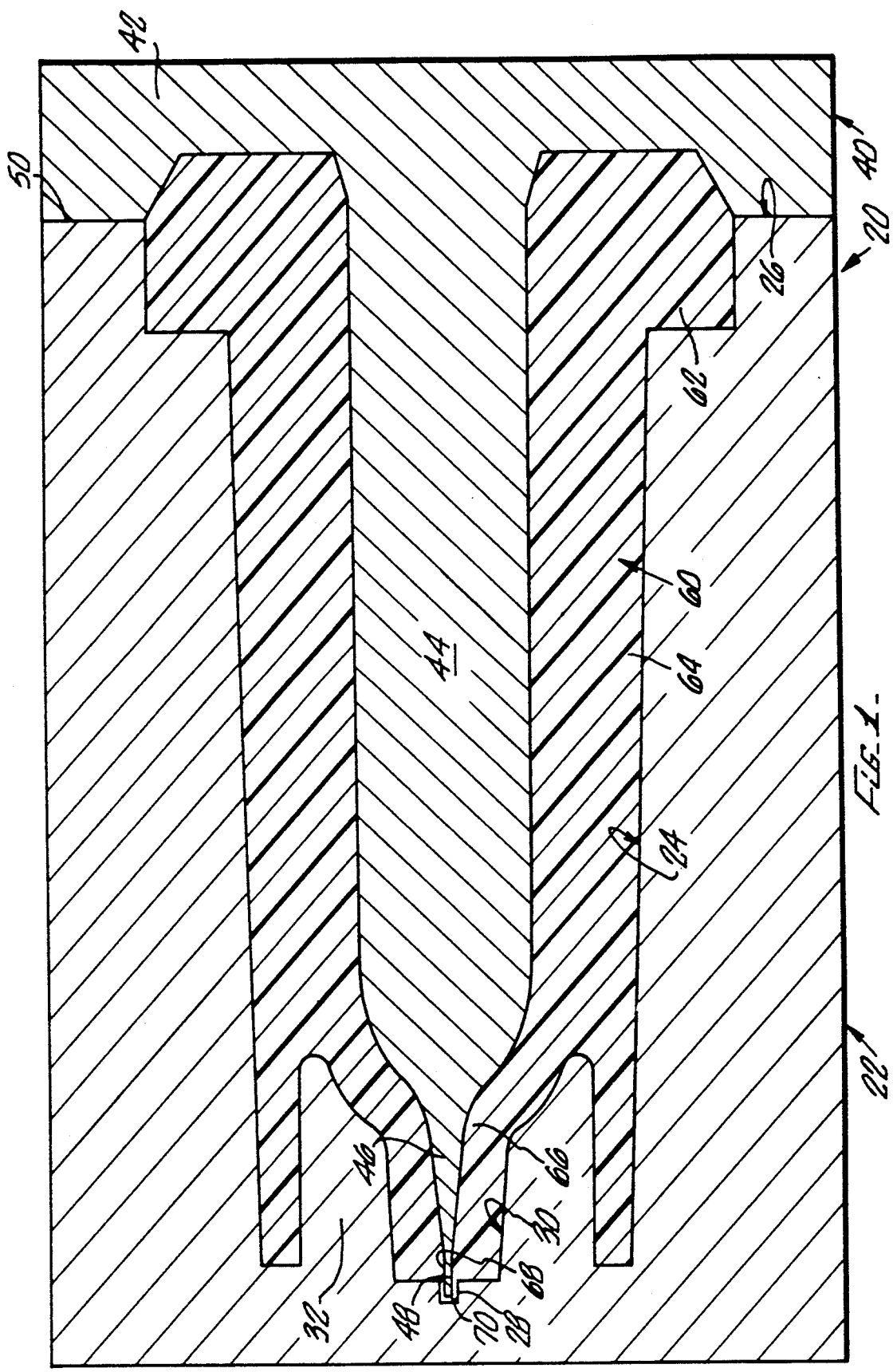
FIG. 1 is a section view of the present mold in the closed position.

As shown in FIG. 1 a mold 20 for injection molding an ampule includes a mold cavity housing 22 having tapered inner cylindrical walls 24 and a back or proximal end 26. At the front end or distal end of the mold 20 is a clearance hole 28 concentrically positioned within a nose bore 30 formed by a distal ring 32.

A core pin 40 has a base 42 and a slightly tapered elongate cylindrical body 44. A generally conical core pin neck 46 extends forwardly from the body 44 and tapers down to a cylindrical core pin tip 48. The core pin base 42 and the mold cavity housing 22 come together at a parting line 50.

As shown in FIG. 1 the mold 20 shapes injected thermoplastic into an ampule 60. The ampule 60 formed by the mold 20 has lugs 62 at the back or proximal end. An ampule body 64 is formed inbetween the mold cavity housing 22 and the core pin body 44. A throat section 66 of the ampule 60 is formed inbetween the core pin neck 46 and the distal ring 32.

Figure 2:
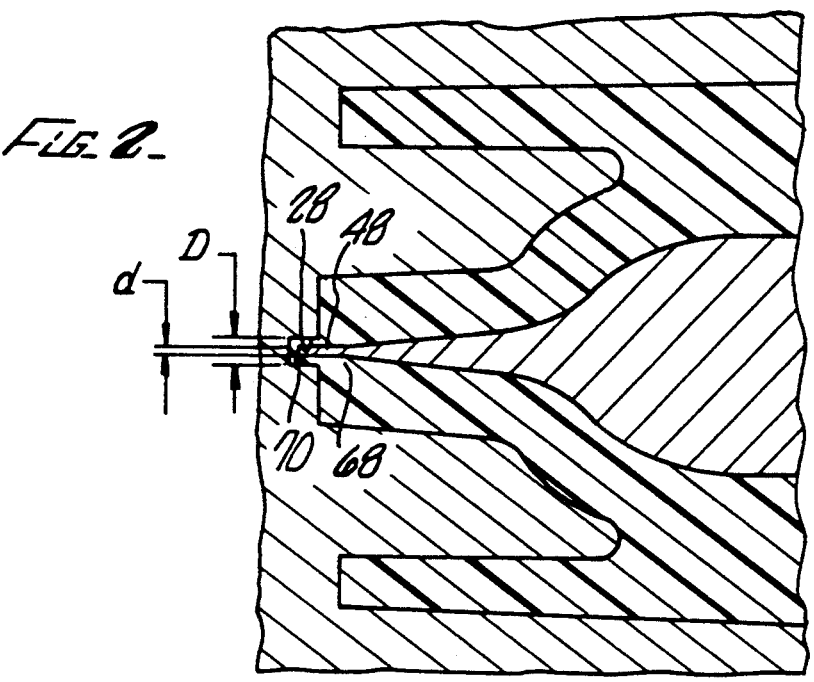
FIG. 2 is an enlarged section view fragment of the mold of FIG. 1.

Turning to FIG. 2, the core pin tip 48 in combination with the distal ring 32 and clearance hole 28 form a nozzle 68 in the ampule 60. The nozzle 68 is surrounded and occluded by a vestigial nozzle pilot cylinder 70.

In use, the core pin tip 48 is piloted or guided into the clearance hole 28 which is made sufficiently large to prevent the core pin tip 48 from hitting the sides of the clearance hole 28 during closure of the mold, as well as during injection of the plastic. Injected plastic flows into the space between the core pin tip 48 and the clearance hole and forms the vestigial nozzle pilot cylinder 70 at the front of the ampule. The ampule is removed from the mold. In a secondary cutting operation, the nozzle pilot cylinder 70 is cut off, thereby exposing the nozzle 68 and producing a finished ampule. The cost of cutting off the nozzle pilot cylinder 70 to expose the nozzle 68 is low and does not significantly add to the cost of the final ampule. This mold and molding method helps to prevent breakage of the core pin tip 48 by avoiding the need to pilot the core pin tip into a tight-fitting pilot hole in the mold cavity housing 22.

Figure 3:
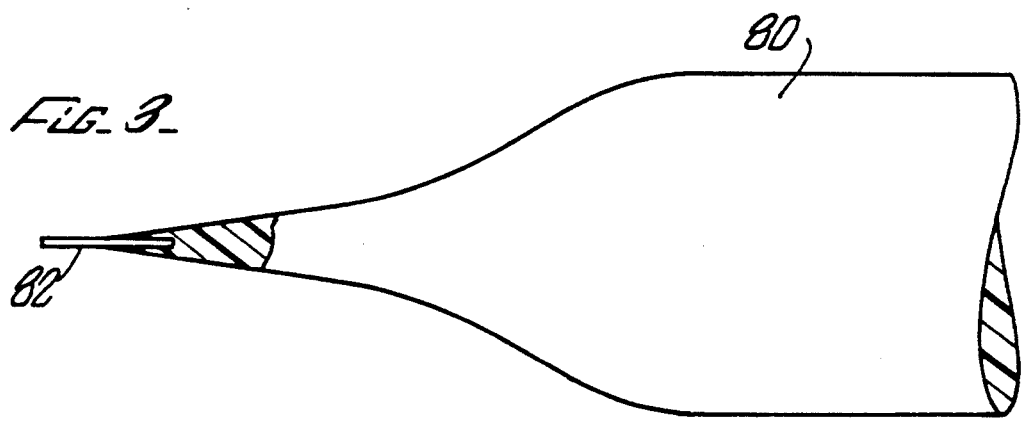
FIG. 3 is a section view fragment of a second embodiment of a core pin.

FIG. 3 shows a core pin 80 constructed with a tip 82 of drawn wire which is welded to the core pin 80. The drawn wire tip 82 has very high tensile strength and is less susceptible to breakage from bending because it is less brittle than a machined core tip. The wire core pin tip also allows use of core pin materials other than tool steel that have improved strength characteristics that elevated temperature, such as tungsten wire. The core pin 80 may be used in a conventional ampule mold, i.e., a mold having a very close clearance pilot hole, or it may also be used in the mold 20 as shown in FIG. 1, or as shown in FIG. 2.

Figure 4:
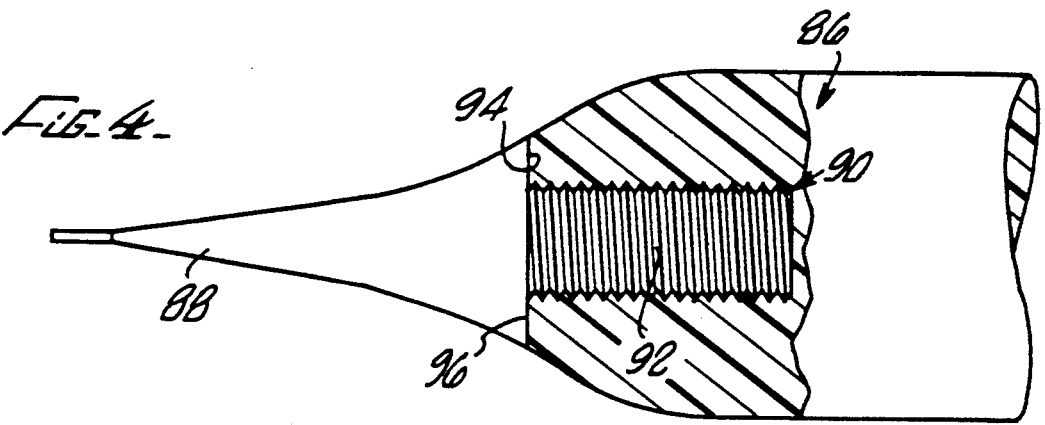
FIG. 4 is a section view fragment of a third embodiment of a core pin.

Turning to FIG. 4, a core pin 86 has a threaded hole 90 at its flat distal face 96. A replaceable core pin tip has a threaded stud 92 engageable into the threaded hole 90 in the core pin 86. A flat shoulder 94 seats flush against the flat distal face 96 of the core pin 86, to form a smooth uninterrupted core pin neck. The core pin shown in FIG. 4 may be used in a conventional ampule mold or in the mold 20 shown in FIG. 1.

Figure 5:
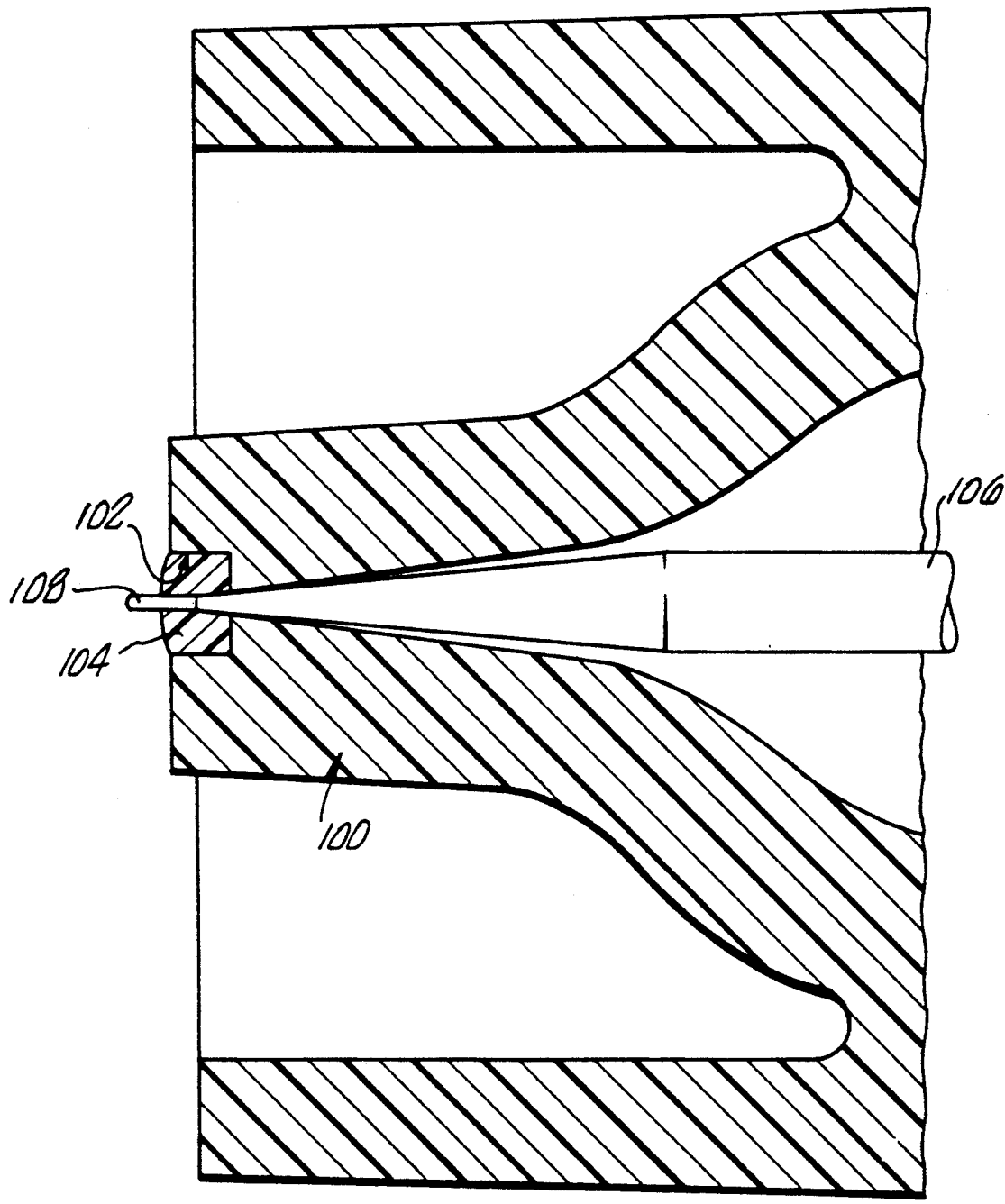
FIG. 5 is an enlarged section view fragment illustrating the present method of casting a nozzle section in an ampule.

FIG. 5 illustrates a mold and method for casting an ampule nozzle in a secondary operation. An ampule 100 has a cup opening 102 at its distal end where the nozzle ordinarily would be located. The cup opening 102 is molded into the ampule 100. After molding, the ampule 100 is ejected or removed from the mold. A tapered pin 106 having pin tip 108 that matches the desired nozzle size and shape is inserted into the cup opening 102 from the proximal end of the ampule. Casting material 104 is introduced into the cup opening 102 and is solidified or cured. The tapered pin 106 is withdrawn leaving a cast nozzle. This mold and method allows the ampule 100 to be molded at low cost and without tool breakage. The casting material may use any one of several biocompatible materials such as urethane, epoxy or ultraviolet cured materials. The casting material 104 and the material of the tapered pin 106 are selected to provide good release of the tapered pin 106 from the casting material 104 to avoid breakage of the pin tip 108 due to sticking when the tapered pin 106 is withdrawn. This casting operation may be automated to lower manufacturing costs.

Figure 6:
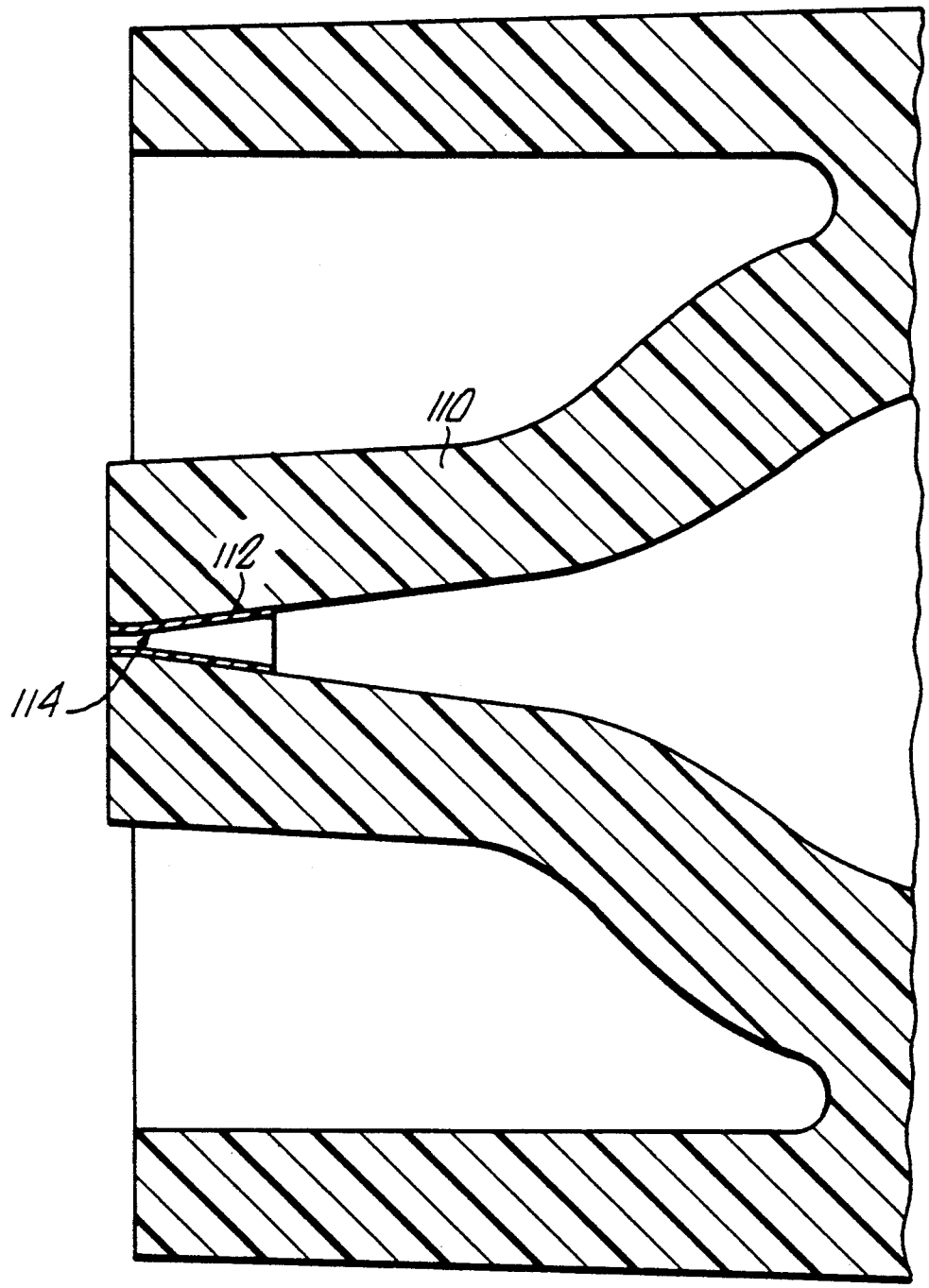
FIG. 6 is an enlarged section view of an ampule having a metal orifice forming the nozzle section.
Figure 7:
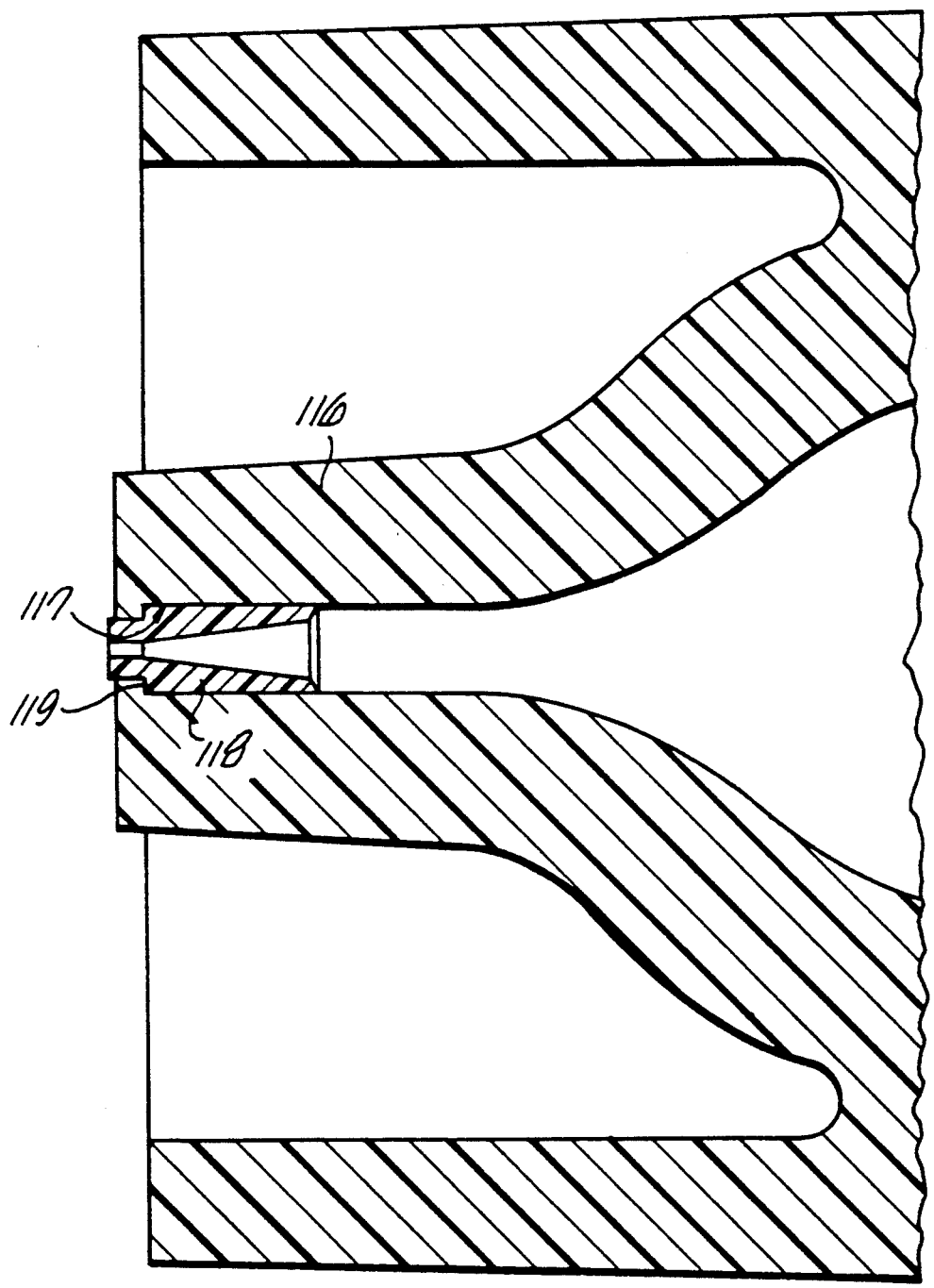
FIG. 7 is a section view fragment of an ampule having a plastic orifice forming the nozzle section.

Referring to FIGS. 6 and 7, with another tool and method, an ampule body is molded with an enlarged opening at its distal end, at the nozzle location, and a separate orifice is installed in a secondary operation which can be automated for low cost. This method allows the ampule body to be molded at low cost without tool breakage, yet still provide the desired nozzle configuration.

As shown in FIG. 6, an ampule 110 is molded with an oversize nozzle 114. An orifice 112 made of formed stainless steel is installed into the oversize nozzle 114 from the proximal or back open end of the ampule 110. The metal orifice 112 is held in place and made leak free by press fitting and the wedge geometry of the oversize nozzle 114.

As shown in FIG. 7, an ampule 116 has an oversize nozzle 117 and a plastic material orifice 118 is press fit into the oversize nozzle 117 from the proximal end of the ampule 116. A shoulder 119 secures the plastic orifice 118 in position.

Preferably, the orifice 118 is made of a plastic that does not stick to tooling as severely as polycarbonate. High strength is not an important criteria in the nozzle section of the ampule because the diameter of the nozzle opening is much less compared to other diameters of the ampule, resulting in less stress on the material during injection. In addition, because the molded plastic orifice 118 is small in size, dimensional control of the pilot hole/core pin registration in the mold (for making the orifice 118) and the molding process is more easily accomplished to allow the pin to be piloted into a pilot hole without striking the edge of the pilot hole. Furthermore, the core pin used in molding the orifice 118 will not deform as much during the injection of the plastic into the orifice mold because the pin is much shorter. This helps to prevent breakage of the pin tip. Molding the orifice 118 as a separate piece allows for use of a single ampule body design that can accommodate various separate orifices, to provide different nozzle shapes and diameters. Molding of the orifice 118 as a separate piece can be accomplished at low cost because the small size of the part allows it to be molded in a mold having a large number of cavities (yet still at low cost) and have very fast molding cycle times.

Figure 8:
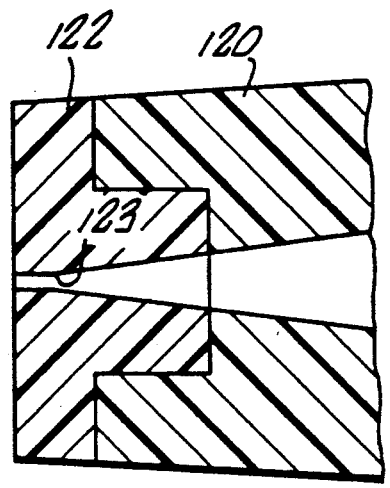
FIG. 8 is an enlarged section view fragment of a rim orifice on an ampule.

As shown in FIG. 8 an ampule 120 has a rim orifice 122 attached at its distal end to form a nozzle 123. The rim orifice 122 has a T-shaped cross section.

Figure 9:
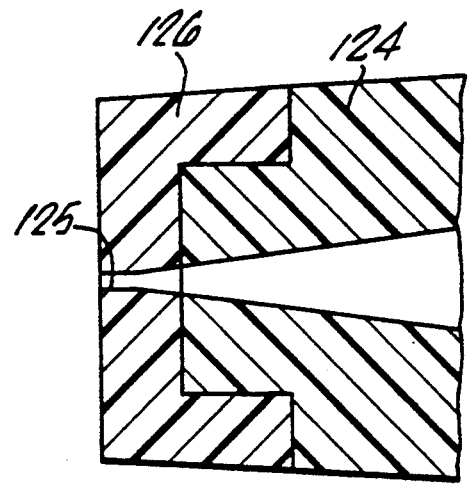
FIG. 9 is an enlarged section view fragment of a cap orifice on an ampule.

Turning to FIG. 9, a cap orifice 126 is attached at the distal end of an ampule 124 to form a nozzle 125.

Figure 10:
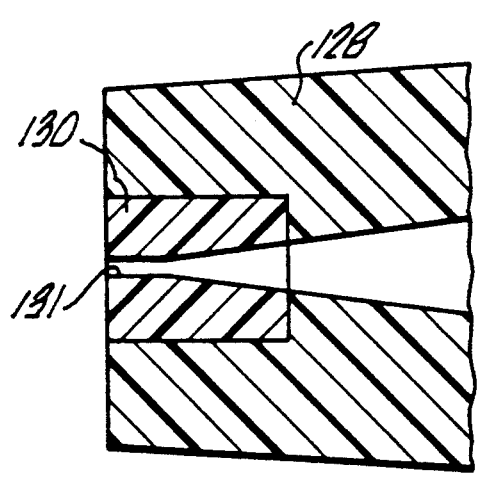
FIG. 10 is an enlarged section view fragment of a plug orifice on an ampule.

As shown in FIG. 10, an ampule 128 is provided with a plug orifice 130 forming a nozzle 131. The separate orifices 122, 126 and 130 in FIGS. 8–10 may be bonded to the complimentary external surfaces of the ampules using adhesives, solvents, sonic welding, heat staking, and other plastic bonding methods.

Figure 11:
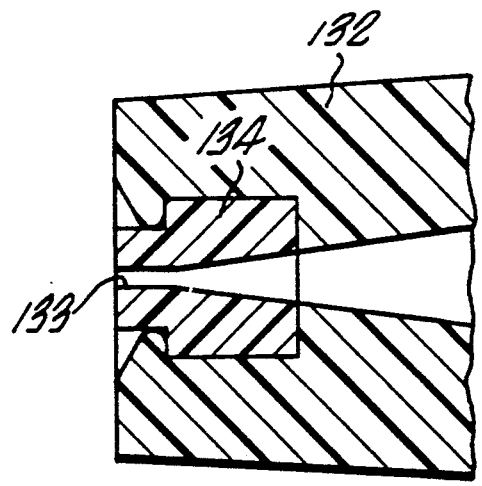
FIG. 11 is an enlarged section view fragment of a shoulder orifice on an ampule.

Turning to FIG. 11, a shoulder orifice 134 is heat staked at the distal end of an ampule 132 forming a nozzle 133.

Thus, while several embodiments and applications of the invention have been shown and described, it would be apparent to those skilled in the art that many more modifications are possible without departing from the inventive concepts herein. The invention, therefore, is not to be restricted except in the spirit of the appended claims.

We claim:

1. In a method of fabricating a nozzle section of a jet injection ampule having a nozzle opening at a front end of the nozzle section, by thermoplastic injection molding of the type using a mold cavity housing and a core pin, and including the steps of moving the core pin into the mold cavity housing to form a mold cavity and injecting thermoplastic into the mold cavity, the improvement comprising the steps of:

guiding a core pin tip on the core pin at least partially into a clearance hole formed by clearance hole walls in the mold cavity housing, without allowing the core pin tip to hit the clearance hole walls, the clearance hole extending beyond the nozzle section of the molded ampule;

allowing the thermoplastic to flow into the clearance hole and around the core pin tip during said injecting step without allowing the core pin tip to hit the clearance hole walls;

allowing the thermoplastic to at least partially solidify and form a nozzle pilot cylinder within the clearance hole and around the core pin tip, with the core pin tip and nozzle pilot cylinder extending beyond the nozzle section;

removing the nozzle section from the mold cavity housing; and removing the nozzle pilot cylinder from the nozzle section to expose the nozzle opening.

2. The method of claim 1 wherein the thermoplastic is polycarbonate.

3. The method of claim 1 wherein the core pin tip is drawn wire.

4. The method of claim 1 wherein the core pin tip is tungsten wire.

5. The method of claim 1 wherein the core pin tip is detachable from the core pin for replacement.

* * * * *